United States Patent [19]

Ufford et al.

[11] Patent Number: 4,951,687
[45] Date of Patent: Aug. 28, 1990

[54] MEDICAL ELECTRICAL LEAD CONNECTOR

[75] Inventors: Keith A. Ufford, Maple Grove; Timothy W. Holleman, Ham Lake, both of Minn.

[73] Assignee: Medtronic, Inc., Minneapolis, Minn.

[21] Appl. No.: 304,756

[22] Filed: Jan. 31, 1989

[51] Int. Cl.⁵ .............................................. A61N 1/05
[52] U.S. Cl. .................................... 128/786; 128/784
[58] Field of Search .................... 128/419 P, 783, 784, 128/785, 786

[56] References Cited

U.S. PATENT DOCUMENTS

| Re. 31,990 | 9/1985 | Sluetz et al. | 128/419 P |
|---|---|---|---|
| 4,106,512 | 8/1978 | Bisping | 128/418 |
| 4,258,725 | 3/1981 | O'Neill | 128/419 P |
| 4,387,727 | 6/1983 | Sandstrom | 128/419 P |
| 4,402,329 | 9/1983 | Williams | 128/785 |
| 4,463,765 | 8/1984 | Gold | 128/785 |
| 4,469,104 | 9/1984 | Peers-Trevarton | 128/419 P |
| 4,577,643 | 3/1986 | Beranek | 128/785 |
| 4,590,950 | 5/1986 | Iwaszkiewicz et al. | 128/419 P |
| 4,628,943 | 12/1986 | Miller | 128/785 |
| 4,667,686 | 5/1987 | Peers-Travarton | 128/785 |

OTHER PUBLICATIONS

Article Entitled "The Impace of Pending Technologies on a Universal Connector Standard", by Doring et al., PACE, vol. 9, pp. 1186-1190, Nov.-Dec. 1986 and exhibit A.

Drawing of the Connector End of an Osypka Model PY-66 Bipolar Screw-In Pacing Lead, Labeled Exhibit B.

Article Entitled "A Voluntary Standard for 3.2 mm Unipolar and Bipolar Pacemaker Leads and Connectors", by Calfee et al., PACE, vol. 9, pp. 1181-1185, Nov.-Dec. 1986.

Primary Examiner—Lee S. Cohen
Assistant Examiner—Kennedy J. Schaetzle
Attorney, Agent, or Firm—Reed A. Duthler; Joseph F. Breimayer

[57] ABSTRACT

A connector for use in conjunction with implantable, medical electrical leads, such as cardiac pacing leads. The connector is of the type known in the pacing industry as "in-line", and includes an elongated connector pin and a cylindrical connector ring, spaced longitudinally from one another, and separated by an insulative segment. The connector pin is adapted to rotate within the connector, in order to transmit torque down the body of the electrical lead to activate a fixation device or other apparatus. Surrounding the connector pin is an elongated bearing sleeve which engages an elongated, reduced diameter segment of the connector pin. The connector pin is provided with circumferential shoulders at the proximal and distal ends of the reduced diameter portion of the pin, which in turn engage the bearing sleeve.

14 Claims, 2 Drawing Sheets

MEDICAL ELECTRICAL LEAD CONNECTOR

BACKGROUND OF THE INVENTION

This invention relates generally to medical electrical leads, and more particularly to implantable medical electrical leads of the type employing in-line, bipolar connectors having rotatable connector pins for transmitting torque along the body of the lead.

An early medical electrical lead with a rotatable connector pin is disclosed in U.S. Pat. No. 4,106,152, issued to Bisping. In the Bisping lead, a unipolar connector was used, the connector being comprised of a conductive connector pin and an insulative sleeve. Both the connector pin and the insulative sleeve were free to rotate relative to the body of the lead. In more modern designs, such as employed in commercially marketed pacing leads, only the connector pin rotated, and the insulative portion of the connector, typically used to seal the lead within the connector housing of an implantable electrical pulse generator, is fixed relative to the body of the lead. Examples of such connector assemblies are shown in U.S. Pat. No. 4,628,943 issued to Miller, U.S. Pat. No. 4,467,687 issued to Peers-Travarton, U.S. Pat. No. 4,577,643 issued to Baraneck, U.S. Pat. No. 4,402,329 issued to Williams, and U.S. Pat. No. 4,463,765 issued to Gold.

While most early screw in leads were unipolar leads, there has been a considerable interest in the development of practical bipolar screw-in leads in the past few years. One such design is disclosed in the Miller patent, discussed above. Other bipolar screw-in leads having in-line connectors include the Medtronic Model 4016 pacing lead and the Osypka PY-66 bipolar screw-in pacing lead. In all three leads, the connector assembly comprises a rotatable connector pin having an exposed length which is intended to be coupled to a first connector attached to a pacemaker, and a connector ring intended to be coupled to a second connector attached to the pacemaker. The exposed portion of the connector ring is separated from the exposed portion of the connector pin by an insulative sleeve, in all three leads.

In the Miller patent, discussed above, the connector pin extends only a short distance into the connector assembly, and is rotatably mounted within the connector assembly by means of a circumferential groove in the pin, located within a corresponding inwardly facing circular ridge in the connector assembly. In the Model 4016, the connector pin is rotatably mounted by means of an expanded diameter section of the connector pin, located coaxially within the insulative member separating the connector pin and connector ring. The expanded diameter portion of the connector pin is retained within the connector assembly by means of a first shoulder, proximal to the ring electrode, within the insulative member and by a second shoulder, proximal to the first shoulder. The insulative member included corresponding inward facing circumferential shoulders, engaging the first and second shoulders of the connector pin. An exploded drawing of the connector of the Model 4016 pacing lead can be found in the article "The Impact of Pending Technologies on a Universal Connector Standard", by Doring, et al, PACE, Vol. 9, pp. 1186-1190, 1986.

In the Osypka lead, the rotating connector pin is also retained within the connector assembly by means of an expanded diameter section of the connector pin, located within the connector assembly. In the Osypka lead, the expanded diameter section is located proximal to the connector ring, at the distal end of the connector pin. The expanded diameter section includes a first circumferential shoulder facing the proximal end of the connector pin, which engages the corresponding distally facing circumferential shoulder in the insulative portion of the connector assembly. It appears that distal movement of the connector pin is prevented only by means of the distal end of the connector pin abutting the proximal end of an insulative sleeve covering the coiled conductor to which the connector pin is attached. The Osypka electrode is notable in that it also includes a metal bearing sleeve located circumferential to the connector pin, proximal to the expanded diameter portion of the pin.

SUMMARY OF THE INVENTION

In the context of an implantable medical electrical lead, especially an implantable pacing lead, reliability and mechanical integrity are of utmost importance. In addition, the increasing trend towards miniaturization has imposed severe size constraints upon the manufacture of medical electrical leads. This has been reflected by the recent trend in the pacing industry to move toward a particular connector configuration standard, known as the "IS-1" standard (formerly the "VS-1" standard). If a manufacturer wishes his pacemaker and leads to be compatible with those of other manufacturers, their connector assemblies must meet this standard. This standard is set forth in the article entitled "A Voluntary Standard For 3.2 mm Unipolar and Bipolar Pacemaker Leads and Connectors", by Calfee, et al, PACE, Vol. 9, pp. 1181-1185, 1986, incorporated herein by reference in its entirety.

In bipolar, in-line connector assemblies employing rotating connector pins, it is desirable to produce as rigid an assembly as is possible, so that the connector pin is not readily deflected relative to the connector ring, and it is similarly desirable to provide a connector pin which rotates as freely as possible, without sticking or binding. The present invention attempts to accomplish all of these goals, within the constraints set by the IS-1 standard.

The IS-1 standard requires the location of resilient sealing rings intermediate the connector ring and connector pin. Typically, these are fabricated of silicone rubber. Given the size constraints associated with the connector assembly, this complicates the problem providing an adequately rigid assembly. In the Oscor lead discussed above, this problem is addressed by providing a metal bearing sleeve, located distal to the connector ring, over which the resilient sealing rings are mounted. Because neither the bearing sleeve nor the connector pin extends within the connector ring, the connector assembly depends upon a molded plastic spacer to retain the connector pin and connector ring in proper alignment.

In the present invention, the connector pin includes a reduced diameter segment which extends for a substantial distance interior to the connector assembly, and at least extends within the connector assembly to the point where it is concentric with the connector ring. An elongated bearing sleeve is provided which extends generally from the point the connector pin exits the connector assembly to a point at least sufficiently far distal to be located concentrically within the connector ring. Connection of the inner conductor to the connector pin occurs at the distal end of the connecor pin.

This construction provides several advantages. First, it provides an extremely rigid structure. Second, it provides an extremely long bearing surface, providing for smooth rotation of the connector pin. Because of the length of the bearing surface, the possibility for the pin binding due to deflection from the axis of the lead is substantially reduced. Third, because the connection of the conductor coil to the connector pin occurs at the distal end of the pin, the diameter of the pin in the area of the bearing sleeve can be reduced. This allows for the increased thickness necessary to locate a hard plastic bearing sleeve within the resilient sleeve which carries the sealing rings.

Use of a plastic bearing sleeve rather than a metal bearing sleeve is believed advantageous. Because it is insulative, it can be extended within the connector ring without compromising electrical isolation of the connector pin and ring. The plastic bearing sleeve is adhesively bonded to the sheath covering the inner conductor to which the connector pin is coupled. This provides an effective fluid seal between the connector pin and connector ring, particularly when the bearing sleeve and the sheath are made of the same type of material, e.g. polyurethane. In addition, use of a plastic bearing sleeve avoids any possibility of generation of spurious electrical signals, due to relative movement of the connector pin and bearing sleeve.

DETAILED DESCRIPTION OF THE INVENTION

Figure 1:
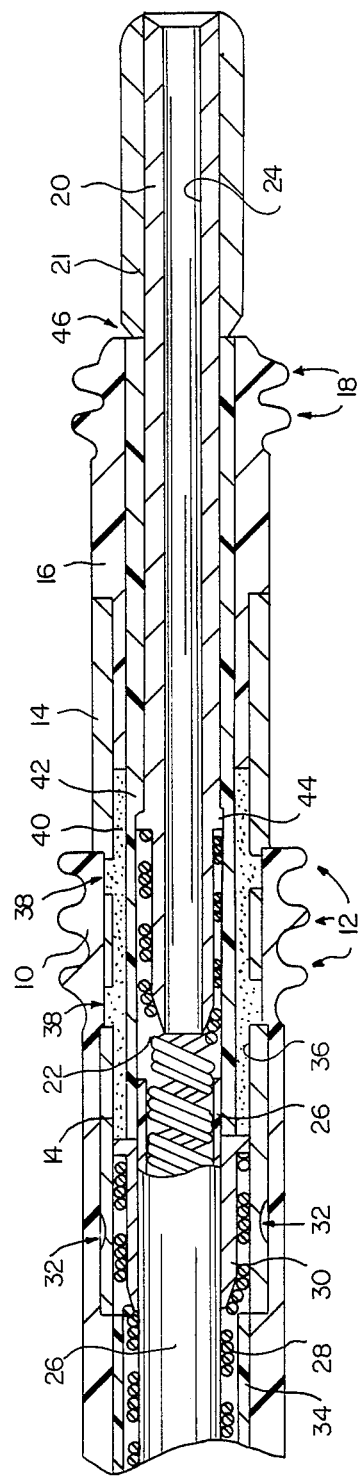
FIG. 1 is a side, cutaway view of a first embodiment of a connector assembly according to the present invention.

FIG. 1 shows a side, cutaway view of a connector assembly according to the present invention. Externally, the connector is configured to conform with the IS-1 connector standard, as applied to bipolar leads, and therefore, displays an insulative sleeve 10, which bears circumferential sealing rings 12. The outer diameter of sealing rings 12 is approximately 0.155". Exposed to the exterior of the connector proximal to insulative sheath 10 is a connector ring 14, which is adapted to contact a corresponding internal electrical connector attached to an implantable pacemaker or other electromedical device. The outer diameter of connector ring 14 is approximately 0.105". A second insulative sheath 16 is exposed to the exterior of the connector proximal to connector ring 14. Insulative sheath 16 displays two circumerential sealing rings 18, which have a diameter of approximately 0.125". Exposed to the exterior of the connector proximal to insulative sheath 16 is a connector pin assembly, comprising an inner connector pin 20 and an outer connector pin 21. Outer pin 21 is welded or crimped to inner pin 20. The outer surface of outer connector pin 21 is adapted to contact a corresponding electrical connector surface mounted to the implantable pacemaker or other electromedical device, and has an outer diameter of approximately 0.062".

Typically, the connector assembly located on the pacemaker takes the form of a bore having connectors arranged lineally therein. In this case, sealing rings 12 seal the entry of the bore to body fluid entry. Sealing rings 18 prevent any body fluid which does enter the bore from forming a conductive pathway between connector ring 14 and outer connector pin 21, which might interfere with the functioning of the pacemaker or the lead.

The connector pin assembly is mounted rotatably within the connector assembly, and is used to rotate a coiled conductor 22. Typically, conductor 22 would be coupled to an extendable fixation screw or electrode, or other mechanical apparatus requiring activation at the distal end of the lead. Extending through internal connector pin 20 is a lumen 24, which is aligned with the lumen of coil 22, to permit passage of a stylet down the lead, in order to direct the lead during implantation.

Surrounding coiled conductor 22 is an insulative sheath 26, which insulates conductor 22 from a second coiled conductor 28, which likewise extends along the length of the lead. Coiled conductor 28 is coupled to connector ring 14 by means of a crimping core 30. Crimps 32 hold conductor 28 mechanically between crimping core 30 and connector ring 14. Surrounding coiled conductor 28 is a second insulating sheath 34, which extends the length of the lead, typically terminating at a ring electrode to which conductor 28 may be coupled. Within connector ring 14 is a lumen 36, connected to the exterior of connector ring 14 by means of perpendicular bores 38. Bores 38 allow the use of backfilling 40, typically silicone rubber based medical adhesive or other adhesive, to interconnect insulative sleeve 10, connector ring 14, and a bearing sleeve 42.

Coiled conductors 22 and 28 may be MP35N, Elgiloy ® alloy, drawn brazed strand or other biocompatible metal. Sheaths 26 and 34 may be silicone rubber, polyurethane or other biocompatible plastic. Sleeves 10 and 16 are preferably silicone rubber. Coiled conductor 22 is coupled to internal connector pin 20 by laser welding, resistance welding, or the like.

Bearing sleeve 42 is an elongated tubular member, typically of a hard plastic having a relatively low coefficient of friction, such as Teflon ®, nylon, or polyurethane. Inner connector pin 22 is mounted rotatably within bearing sleeve 42, and is retained within bearing sleeve 42 by a distal shoulder 44, and by a proximal shoulder 46, formed by the distal end of outer connector pin 21. This structure provides an elongated bearing surface, minimizing the chance for binding of the connector pin assembly. In addition, this structure provides substantial additional rigidity to the connector assembly. It should be noted that bearing sleeve 42, in this embodiment, extends from the point at which the connector pin assembly emerges from the proximal end of the connector assembly, back to a point distal to sealing rings 12. Most importantly, it extends a substantial distance within connector ring 14. This overlap provides for a rigid structure which extends essentially from the distal end of connector ring 14, all the way through the proximal end of the connector pin assembly. This is especially valuable, in that it minimizes the potential for damage of the connector assembly when inserted in the pacemaker, while allowing the free rotation of the connector pin assembly and conductor before insertion into the cardiac pacemaker. Bearing sleeve 42 is adhesively bonded to inner sheath 26 to provide a fluid seal between the connector pin 20, 22 and the connector ring 14.

Figure 2:
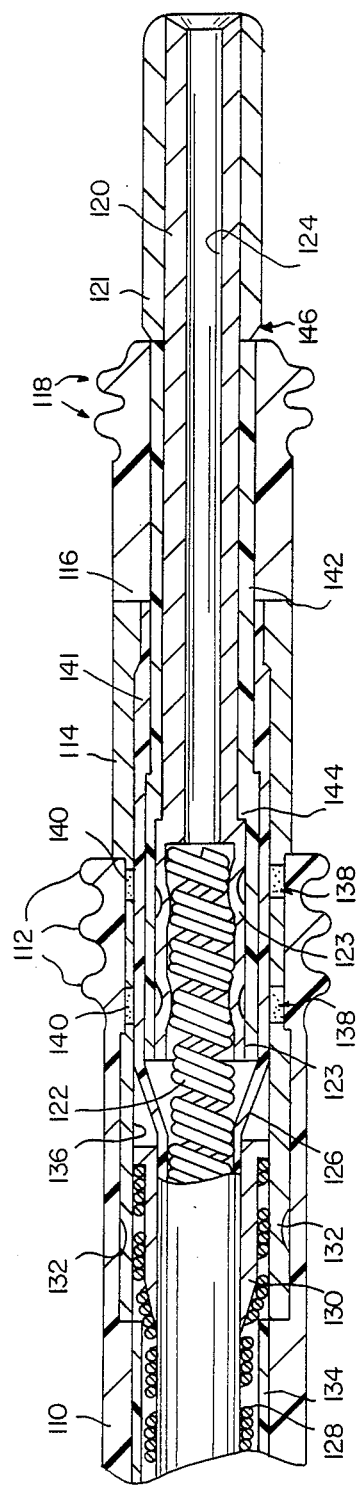
FIG. 2 is a side, cutaway of a second embodiment of a connector assembly according to the present invention.

FIG. 2 shows a side cutaway view of a second embodiment of the connector assembly according to the present invention. Like the connector assembly illustrated in FIG. 1, this connector assembly has an exterior configuration which conforms to the IS-1 connector standard. An outer insulative sleeve 110 is located at the distal end of the connector assembly, and includes three circumferential sealing rings 112. Exposed to the exterior of the connector assembly proximal to insulative sleeve 110 is a connector ring 114, functioning similar to the connector ring 14 discussed in conjunction with FIG. 1 above. Exposed to the exterior of the connector assembly proximal to connector ring 114 is a second insulative sleeve 116, which includes sealing rings 118. Insulative sleeve 116 and sealing rings 118 function as described in conjunction with corresponding structure in FIG. 1, above. Exposed to the exterior of the proximal end of the connector assembly is a connector pin assembly which comprises an inner connector pin 120 and an outer connector pin 121. The connector pin assembly is mounted rotatably within the connector assembly, and is used to rotate an elongated coiled conductor 122, which extends to the distal end of the lead, and is used to activate a mechanical device, such as an extendable fixation screw or electrode.

The embodiment of FIG. 2 differs from the embodiment of FIG. 1 in several respects. Most notably, conductor 122 is coupled to the interior of inner connector pin 120, rather than to the exterior of the connector pin, as illustrated in FIG. 1. Conductor 112 is electrically and mechanically joined to inner connector pin 120 by means of crimps 123. Inner connector pin 120 is provided with a cylindrical lumen 124, which is aligned with the inner lumen of conductor coil 122, allowing for passage of the stylet along the length of the lead. Surrounding conductor 122 is an insulative sheath 126. Located external to insulative sheath 126 is a second coiled conductor 128, which is coupled to connector ring 114 by means of a crimping core 130. Conductor 128 is electrically and mechanically coupled to connector ring 114 by means of crimps 132. External to conductor 128 is a second insulative sheath 134, which extends along the length of the lead body, typically terminating at a ring electrode, to which conductor 128 is coupled. Connector ring 114 is provided with two perpendicular bores 138. The bores 138 are backfilled with adhesive 40, to mechanically interlock connector ring 114, insulative sheath 126 and insulative sheath 110. Located within connector ring 114 is a third insulative sleeve, 141.

Mounted within the connector assembly is a bearing sleeve 142, which extends from a point distal to sealing rings 112, all the way to the point at which the connector pin assembly exits the proximal end of the connector assembly. Bearing sleeve 142 is typically manufactured of a hard plastic having a low coefficient of friction, such as Teflon ®, nylon, or polyurethane. The inner connector pin 120 is rotatably mounted within bearing sleeve 142, and is retained within bearing sleeve 142 by means of a shoulder 144 and by means of the shoulder 146 formed by the distal end of outer connector pin 121. This provides an elongated bearing surface, which functions as described in conjunction with the connector pin and bearing sleeve described with regard to FIG. 1, above. Again, this configuration provides a rigid connector assembly with a low frictional resistance to rotation of internal connector pin 120 and conductor 122. In conjunction with this function, it is believed important that the bearing sleeve extend at least distally enough to allow for substantial overlap with connector ring 114. This structure provides the necessary overall rigidity to prevent damage to the connector assembly during insertion into a cardiac pacemaker or other electromedical device The distal end of bearing sleeve 142 is adhesively bonded to the proximal end of inner sheath 126 to provide a fluid seal between connector ring 114 and connector pin 120,122.

In both of the embodiments illustrated above, it should be noted that the connection of the conductor 122 is accomplished distal to the vicinity of the most proximal of the insulative sleeves (e.g. 16, FIG. 1, 116, FIG. 2). This allows the diameter of inner connector pin 120 to be substantially reduced, allowing for the use of a thicker bearing sleeve 142, which in turn facilitates the use of a rigid plastic, rather than a metal bearing sleeve, while remaining within the size constraints of the IS-1 connector standard. It is also important to note that in both embodiments disclosed above, the connector pin assembly is restrained against both proximal and distal movement within the connector block, by means of corresponding proximal and distal shoulders located on the bearing sleeves 42 (FIG. 1), 142 (FIG. 2) and the connector pin assemblies, 20,21 (FIG. 1) and 120,121 (FIG. 2).

While this invention is disclosed in conjunction with a bipolar lead, it should be appreciated that certain features of the invention would also be applicable to a unipolar lead, having the same external configuration, by substitution of a non-conductive member for or revision to connector ring 114, and the deletion of conductor coil 128. In addition, the invention may also be advantageously practiced in conjunction with connector assemblies employing three or more conductive elements, where size constraints are also a problem.

In conjunction with the above specification, we claim:

1. In a medical lead of the type having a proximal end and a distal end and having a connector assembly mounted to the proximal end of said lead, said connector assembly of the type having an exterior surface, a connector ring, an insulative sleeve exposed to the exterior surface of said connector assembly proximal to said connector ring and a rotatably mounted connector pin extending proximal to said insulative sleeve, said connector ring, connector pin and insulative sleeve all having proximal and distal ends and exterior surfaces, said insulative sleeve and said connector ring having interior lumens, the improvement wherein:
   said connector pin extends distally within said insulative sleeve and said connector ring and wherein the distal end of said connector pin terminates distal to the proximal end of said connector ring; and
   wherein said connector assembly further comprises an elongated bearing sleeve having a proximal end and a distal end, said bearing sleeve extending proximally within said insulative sleeve to a point adjacent the proximal end of said insulative sleeve and extending distally to a point distal to the proximal end of said connector ring.

2. An electrical lead according to claim 1 wherein said lead is of the type having an elongated coil conductor rotatably mounted within said lead, said conductor having a proximal end and a distal end and wherein the distal end of said connector pin is coupled to the proximal end of said elongated conductor.

3. A lead according to claim 2 wherein the proximal end of said elongated conductor is mounted to the exterior surface of said connector pin.

4. A lead according to claim 2 wherein said connector pin is provided with an interior lumen open to the distal end of said connector pin and wherein the proximal end of said elongated conductor is mounted within the lumen of said connector pin.

5. In a medical lead of the type having a proximal end, a distal end, an elongated conductor rotatably mounted within said lead and a connector assembly mounted to the proximal end of said lead, said connector assembly of the type having an exterior and comprising a connector ring, an insulative sleeve exposed to the exterior of said connector assembly proximal to said connector ring and a rotatably mounted connector pin extending proximal to said insulative sleeve, said elongated conductor, insulative sleeve, connector ring and connector pin all having exterior surfaces, proximal and distal ends, said connector ring and insulative sleeve having interior lumens, the improvement wherein:

said connector pin extends distally within said insulative sleeve and within said connector ring to a point distal to the proximal end of said connector ring; and wherein said connector pin is coupled to the proximal end of said elongated conductor, said proximal end of said elongated conductor extending proximally to a point proximal to the distal end of said connector ring.

6. A lead according to claim 5 further comprising an elongated bearing sleeve surrounding said connector pin within which said connector pin is free to rotate.

7. A lead according to claim 6 wherein said bearing sleeve has a proximal end and a distal end, the proximal end of said bearing sleeve extending proximally to a point adjacent to the proximal end of said insulative sleeve, the distal end of said bearing sleeve extending distally to the proximal end of said connector ring.

8. A medical lead according to claim 5 wherein said connector pin is provided with a reduced diameter segment extending from a point adjacent the proximal end of said insulative segment and extending distally to a point distal to the proximal end of said connector ring; and wherein said connector assembly further comprises an elongated bearing sleeve surrounding said reduced diameter segment of said connector pin.

9. A medical lead according to claim 8 wherein said elongated conductor takes the form of a coiled conductor and wherein the proximal end of said elongated conductor is coupled to the distal end of said connector pin, the proximal end of said elongated conductor terminating distally to said reduced diameter segment of said connector pin.

10. A medical lead according to claim 8 wherein the proximal end of said elongated conductor is mounted to the exterior surface of said connector pin.

11. A medical lead according to claim 9 wherein said connector pin is provided with an internal lumen open to the distal end of said connector pin and wherein the proximal end of said elongated connector is mounted within said interior lumen of said connector pin.

12. A medical lead according to claim 8 wherein said connector pin is provided with distal and proximal facing circumferential shoulders located adjacent the proximal and distal ends, respectively, of said reduced diameter segment of said connector pin.

13. A medical lead according to claim 12 wherein said bearing sleeve is provided with means for cooperating with said proximal and distal facing circumferential shoulders of said connector pin.

14. A medical lead according to claim 12 wherein said connector pin comprises an inner connector pin and an outer connector pin, said inner connector pin including said reduced diameter section, said outer connector pin mounted circumferentially around said inner connector pin, said outer connector pin forming said distal facing circumferential shoulders adjacent the proximal end of said reduced diameter section of said connector pin.

* * * * *